(12) United States Patent
Govari et al.

(10) Patent No.: US 10,736,509 B2
(45) Date of Patent: Aug. 11, 2020

(54) DUAL FREQUENCY CONTROL FOR A PHYSIOLOGIC MONITOR

(71) Applicant: Biosense Webster (Israel) Ltd., Yokneam (IL)

(72) Inventors: Assaf Govari, Haifa (IL); Yaron Ephrath, Karkur (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 134 days.

(21) Appl. No.: 16/048,542

(22) Filed: Jul. 30, 2018

(65) Prior Publication Data

US 2020/0029812 A1    Jan. 30, 2020

(51) Int. Cl.
A61B 5/00 (2006.01)
H02J 50/00 (2016.01)
A61B 5/0408 (2006.01)
H01M 10/42 (2006.01)

(52) U.S. Cl.
CPC .......... *A61B 5/0006* (2013.01); *A61B 5/0031* (2013.01); *A61B 5/0408* (2013.01); *H01M 10/425* (2013.01); *H02J 50/00* (2016.02); *H01M 2010/4271* (2013.01)

(58) Field of Classification Search
CPC ... A61B 5/0006; A61B 5/0031; A61B 5/0408; A61B 2560/0209; A61B 5/002; A61B 5/0402; A61B 5/14532; A61B 5/14542; A61B 5/686; H01M 10/425; H01M 2010/4271; H02J 50/00; G16H 40/67
See application file for complete search history.

(56) References Cited

U.S. PATENT DOCUMENTS

| 4,785,827 | A | 11/1988 | Fischer |
| 6,456,887 | B1 | 9/2002 | Dudding et al. |
| 6,564,807 | B1 | 5/2003 | Schulman et al. |
| 6,595,927 | B2 | 7/2003 | Pitts-Crick et al. |
| 6,631,290 | B1 | 10/2003 | Guck et al. |
| 6,766,200 | B2 | 7/2004 | Cox |
| 7,206,630 | B1 | 4/2007 | Tarler |
| 8,509,882 | B2 | 8/2013 | Albert et al. |
| 8,684,925 | B2 | 4/2014 | Manicka et al. |
| 8,965,402 | B2 | 2/2015 | Vathsangam et al. |
| 9,186,089 | B2 | 11/2015 | Mazar et al. |

(Continued)

OTHER PUBLICATIONS

Extended European Search Report dated Jan. 2, 2020 for the European Patent Application No. 19188872.6.

(Continued)

*Primary Examiner* — George Manuel
(74) *Attorney, Agent, or Firm* — Volpe and Koenig, P.C.

(57) ABSTRACT

A physiologic monitoring device is configured to detect and record signals from the sensor and to wirelessly communicate via the communication interface with a transmitter and a receiver that are disposed outside the housing, and to receive via the communication interface transmissions of commands and data from the transmitter. The device operates in a standby mode and an active mode Transmissions comprise control signals to change the mode of operation that are transmitted by the transmitter at a first frequency in a range of 1-10 GHz, and transfers of recorded data from the sensor to the receiver in a range of 400-450 MHz.

22 Claims, 4 Drawing Sheets

(56) References Cited

U.S. PATENT DOCUMENTS

| | | |
|---|---|---|
| 9,215,075 B1 | 12/2015 | Poltorak |
| 2001/0031998 A1 | 10/2001 | Nelson et al. |
| 2002/0138009 A1 | 9/2002 | Brockway et al. |
| 2005/0182389 A1 | 8/2005 | LaPorte et al. |
| 2006/0290496 A1 | 12/2006 | Peeters |
| 2007/0150019 A1 | 6/2007 | Youker et al. |
| 2010/0228135 A1 | 9/2010 | Schulhauser et al. |
| 2010/0262029 A1 | 10/2010 | Kelly et al. |
| 2010/0292556 A1 | 11/2010 | Golden |
| 2011/0093287 A1 | 4/2011 | Dicks et al. |
| 2011/0178375 A1 | 7/2011 | Forster |
| 2011/0202103 A1 | 8/2011 | Wikman et al. |
| 2011/0288379 A1 | 11/2011 | Wu |
| 2012/0191147 A1 | 7/2012 | Rao et al. |
| 2013/0030259 A1 | 1/2013 | Thomsen et al. |
| 2014/0142403 A1 | 5/2014 | Brumback et al. |
| 2014/0156308 A1 | 6/2014 | Ohnemus et al. |
| 2014/0228649 A1 | 8/2014 | Rayner et al. |
| 2014/0288435 A1 | 9/2014 | Richards et al. |
| 2016/0045169 A1 | 2/2016 | Mazar et al. |
| 2017/0250561 A1 | 8/2017 | Li et al. |
| 2017/0251390 A1 | 8/2017 | Gold et al. |
| 2017/0259072 A1 | 9/2017 | Newham et al. |
| 2017/0312530 A1* | 11/2017 | Schilling ............... H04L 67/125 |

OTHER PUBLICATIONS

Chang et al., "Novel Triple-Band Biotelemetry System with Miniaturized Antenna for Implantable Sensing Applications." SENSORS, 2010 IEEE, Kona, HI, 2010, pp. 104-107. (2010).

* cited by examiner

DUAL FREQUENCY CONTROL FOR A PHYSIOLOGIC MONITOR

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to remote physiological monitoring using telemetry. More particularly, this invention relates to wireless communication with an injectable cardiac monitor.

2. Description of the Related Art

The meanings of certain acronyms and abbreviations used herein are given in Table 1.

TABLE 1

| Acronyms and Abbreviations | |
|---|---|
| ECG | Electrocardiogram |
| ICM | Insertable Cardiac Monitor |
| ISM | Industrial, Scientific and Medical |
| MICS | Mobile Information and Communication Systems |
| NFC | Near Field Communication |
| NVM | Non-Volatile Memory |
| RF | Radio Frequency |
| RFID | Radio Frequency Identification |
| SPI | Serial Peripheral Interface |
| SRAM | Static Random Access Memory |

Various sorts of implantable monitoring devices are known in the art. ("Implantable" in this context includes devices that are inserted under the patient's skin, as well as deeper inside the body.) For example, Medtronic (Minneapolis, Minn.) produces the Reveal™ XT Insertable Cardiac Monitor (ICM), which is implanted under the skin of the chest and captures ECG information that can be useful in diagnosing cardiac arrhythmias. The ICM transfers data on demand via wireless link to a nearby receiver.

There have been a number of suggestions in the patent literature to provide implantable medical devices with generic wireless interfaces, enabling communication with standard sorts of communication devices, such as smartphones. For example, U.S. Pat. No. 9,215,075 describes systems and methods for supporting encrypted communications with a medical device, such as an implantable device, through a relay device to a remote server. An implantable medical device is generally constrained to employ a low-power transceiver, which supports short-distance digital communications. A relay device, such as a smartphone or Wi-Fi access point, acts as a conduit for the communications to the internet or other network. The medical device negotiates a secure channel through a smartphone or router, for example, which provides application support for the communication, but may be isolated from the content.

SUMMARY OF THE INVENTION

There is provided according to embodiments of the invention a physiologic monitoring device including a housing that is adapted for implantation in a body of a patient and containing a communication interface, a sensor responsive to a physiologic event, a processor. The processor is configured to detect and record signals from the sensor and to wirelessly communicate via the communication interface with a transmitter and a receiver that are disposed outside the housing, and to receive via the communication interface transmissions of commands and data from the transmitter. The device includes a memory accessible to the processor and a battery for powering the device, wherein the device operates in one of a standby mode and an active mode that consumes more power from the battery than the standby mode, The transmissions comprise control signals that are transmitted by the transmitter at a first frequency in a first range of 1-10 GHz, and transfers of recorded data from the sensor to the receiver at a second frequency in a second range of 400-450 MHz.

According to an aspect of the device, the control signals comprise a wakeup command to terminate the standby mode and to begin operation in the active mode.

According to another aspect of the device, the control signals comprise a command to enter the standby mode of operation.

According to a further aspect of the device, the control signals comprise a command to receive program modifications.

According to yet another aspect of the device, the control signals comprise a command to initiate or terminate monitoring of signals from the sensor.

According to still another aspect of the device, the control signals comprise a signal to transfer data from the memory to the receiver.

According to a further aspect of the device, the first frequency is 2.4 GHz.

According to yet another aspect of the device, the second range is 402-MHz-405-MHz.

According to an additional aspect of the device, the second range is 433-MHz-434-MHz.

According to still another aspect of the device, the physiologic event is an electrical signal from a heart of the patient.

An additional aspect of the device includes battery charging circuitry linked to the battery.

According to another aspect of the device, the control signals comprise a command to activate the battery charging circuitry to charge the battery.

There is further provided according to embodiments of the invention a method of physiologic monitoring, which is carried out by providing a device that is adapted for implantation in a body of a patient. The device includes a housing, a communication interface, a sensor responsive to a physiologic event, and a processor, which is configured to detect and record data from the sensor. The device includes a memory accessible to the processor, and a battery for powering the device. The method is further carried out by operating the device in one of a standby mode and an active mode that consumes more power from the battery than the standby mode, wirelessly exchanging signals via the communication interface with a transmitter and a receiver that are disposed outside the housing. Exchanging signals comprises: when the device is in the standby mode receiving control signals from the transmitter at a first frequency in a first range of 1-10 GHz to terminate the standby mode and to begin operation in the active mode, and when the device is in the active mode at a second frequency transferring the recorded data in a second range of 400-450 MHz from the sensor to the receiver, and receiving program instructions from the transmitter to operate the processor.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
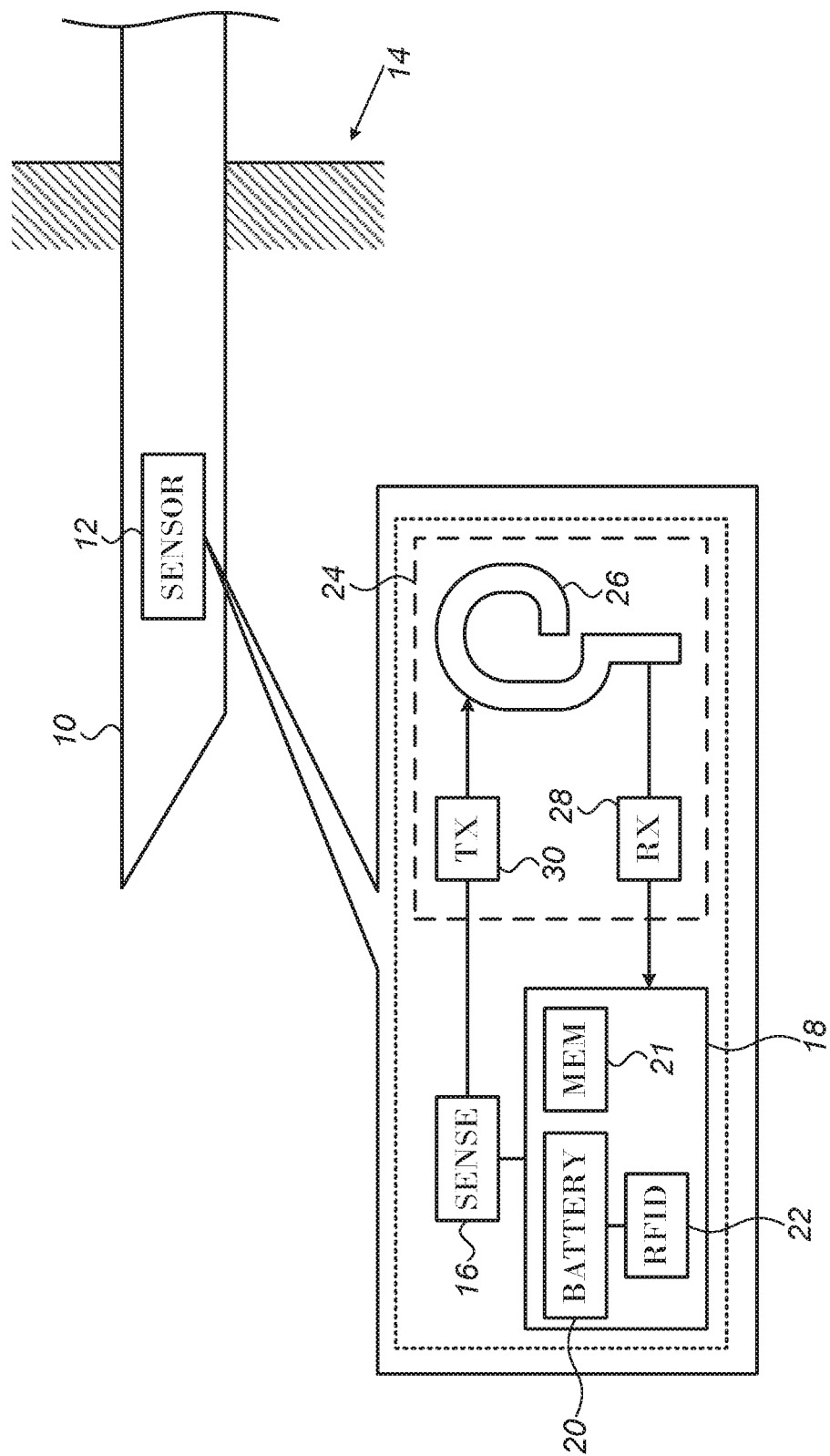
FIG. 1 is a schematic diagram illustrating introduction of a physiologic monitor in accordance with an embodiment of the invention.

Turning now to the drawings, Reference is initially made to FIG. 1, which is a schematic diagram illustrating introduction of a physiologic monitor in accordance with an embodiment of the invention. In this embodiment a needle 10 is used to inject a sensor 12 into subcutaneous issues 14 of a subject. Typically the sensor 12 is a sealed package, e.g., ceramic-coated, which is about 2 mm wide and about 2 cm in length. Sealing may be accomplished, for example, using the methods disclosed in U.S. Pat. No. 4,785,827, entitled Subcutaneous Housing Assembly, which is herein incorporated by reference.

The method of introduction shown in FIG. 1 is exemplary, and the sensor 12 can be introduced into various body tissues by many known techniques, such as a catheter, endoscope, or injection gun, without or without imaging control. In one embodiment the device can be placed subcutaneously with a 5-8 mm incision. Alternatively, the sensor 12 can be secured within the wall of the left ventricle of the heart using a corkscrew, helical anchor, a harpoon, a threaded member, a hook, a barb, a fastener, a suture, or a mesh or coating for receiving fibrous tissue growth.

The sensor 12 may be tailored to detect and monitor a variety of physiological systems, such as cardiac or neural electrophysiology. In embodiments the sensor 12 may comprise an electrode or electrodes, which senses and records physiological activity, such as cardiac electrical signals. Additionally or alternatively the sensor 12 may record data such as left ventricular blood pressure, or chemistries, such as oxygen saturation, glucose levels, therapeutic drug levels, and many more. In some embodiments the sensor 12 may be provided logical circuitry 16 (SENSE) having sufficient analytical capabilities to analyze the electrical signals and characterize cardiac arrhythmias. The circuitry 16 in the sensor 12 may detect and measure more than one parameter.

A power-supply 18 that powers the circuitry 16 includes a battery, which can be rechargeable battery 20 and RFID-based battery charging circuitry 22 that is responsive to a charging signal delivered from a remote transmitter. Suitable apparatus for the battery charging circuitry 22 is disclosed in U.S. Patent Application Publication No. 2010/0262029 by Kelly et al., entitled Needle Implantable Atrial Fibrillation Monitor And Methods For Use Therewith, which is herein incorporated by reference.

The sensor 12 comprises a wireless communication system 24 enabling it to be remotely activated and configured, and to download data on command or autonomously to a remote receiver. The communication system 24 includes antenna 26, receiver 28 and short range transmitter 30, which can be implemented in a single unit as a transceiver or as separate modules as shown in FIG. 1. A suitable memory 21 is provided for storage of program instructions and data obtained from the circuitry 16.

Figure 2:
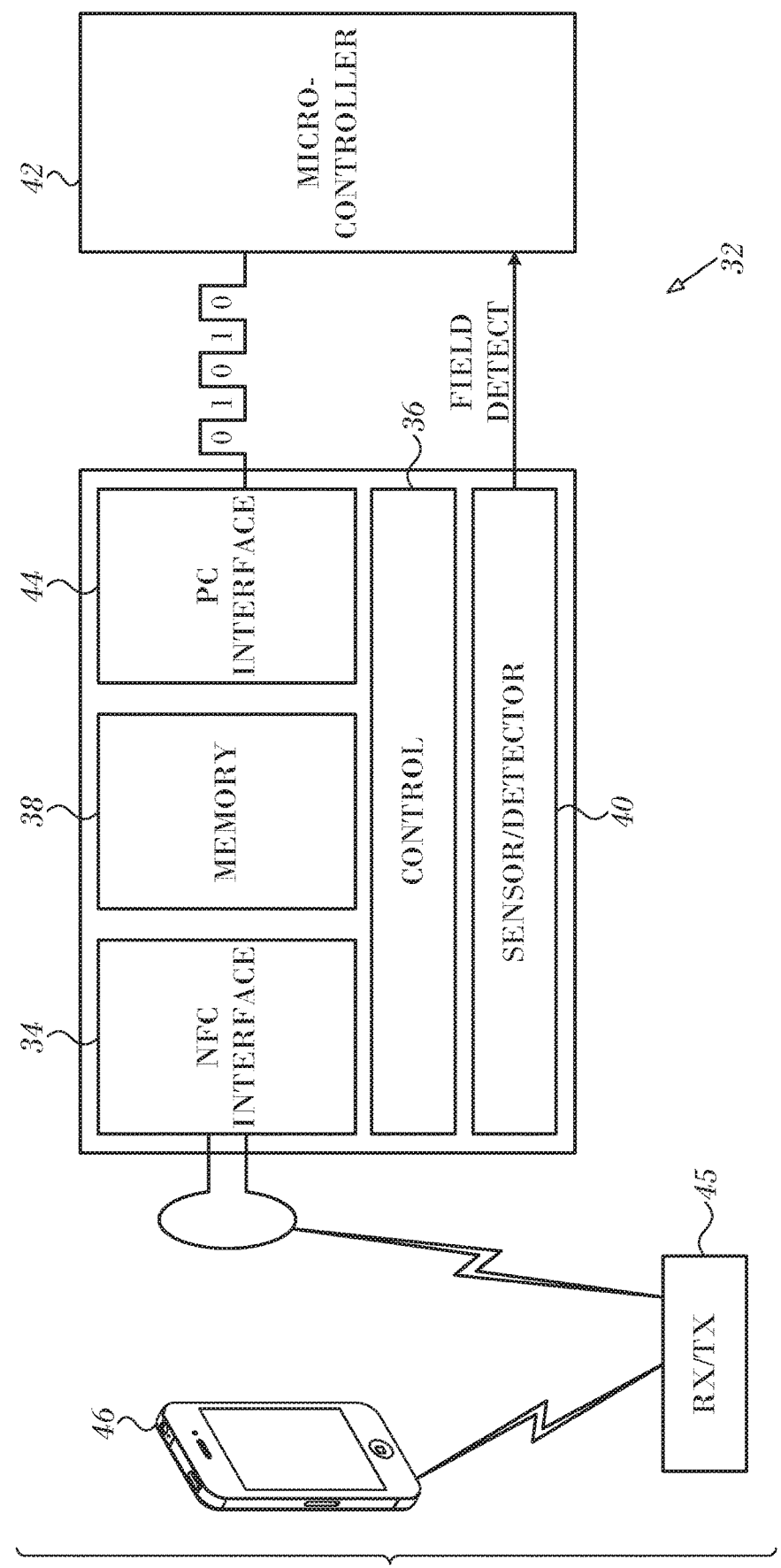
FIG. 2 is a block diagram of circuitry that is included in an injectable or implantable physiologic monitor, in accordance with an embodiment of the invention.

Reference is now made to FIG. 2, which is a block diagram of circuitry that is included in an injectable or implantable physiologic monitor 32, in accordance with an embodiment of the invention. The physiologic monitor 32 carries out the functions of the circuitry 16 and battery charging circuitry 22 in the sensor 12 (FIG. 1). The physiologic monitor 32 includes a near field interface 34, control processor 36 having a system clock (not shown), a memory 38 that is accessible to the processor 36 for storing control instructions and data obtained from a sensor or detector 40. A microcontroller 42 is linked to other components of the physiologic monitor 32 by an interface 44, which could be a serial peripheral monitor 32 may be activated by a remote transceiver 86, which can be linked to and controlled by a suitably configured smartphone 46, e.g., via Bluetooth®.

Figure 3:
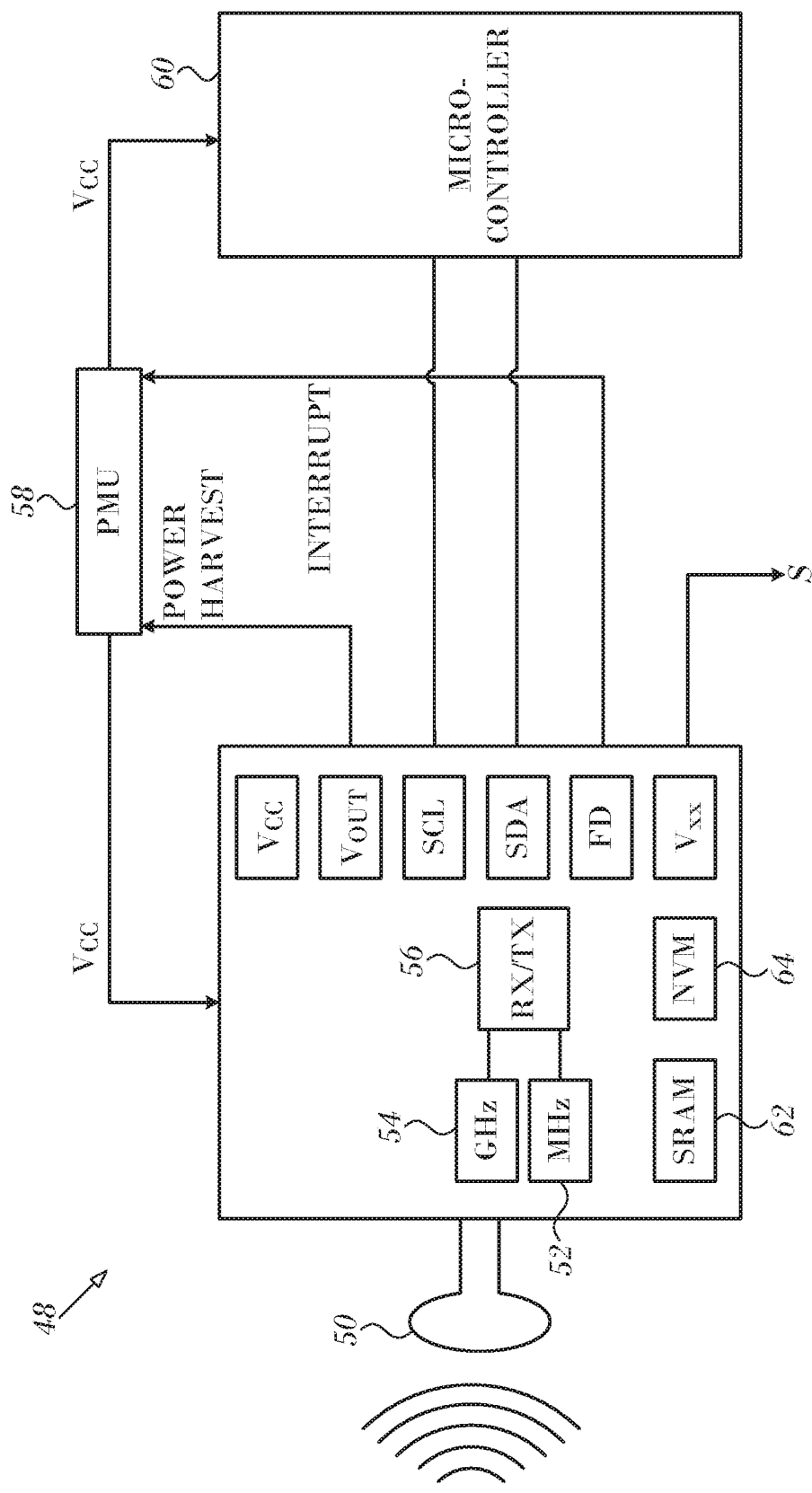
FIG. 3 is a block diagram of circuitry 48 that can be included in an injectable or implantable physiologic monitor, in accordance with an embodiment of the invention.

FIG. 3 is a block diagram of circuitry 48 that can be included in an injectable or implantable physiologic monitor, in accordance with an embodiment of the invention. The inventors have discovered that power economies in the physiologic monitor can be achieved using dual frequencies: a relatively high frequency, i.e. 1-10 GHz, e.g., 2.4 GHz, is employed for control functions, e.g., to awaken the monitor from a standby mode, and to initiate or discontinue monitoring and battery charging. Telemetry and transfer of data is performed using a relative low frequency in the industrial, scientific and medical spectrum (ISM): 402-405 MHz (10 MICS-band channels) and 433-434 MHz (2 ISM-band channels). The circuitry 48 includes an antenna 50 and, tuners 52, 54 for the low and high frequencies, respectively. The tuners 52, 54 are connected to a conventional digital transceiver 56. The Implant Module Model ZL70323MN, available from Microsemi Corp, Aliso Viejo, Calif. USA 92656 is suitable for the transceiver 56.

A power management unit 58, including charging circuitry is linked to the transceiver 56, which feeds power derived from the low frequency signal and the tuner 52. As in the embodiment of FIG. 2 the operations of the circuitry 48 are regulated by a microcontroller 60. Unlike the embodiment of FIG. 2, the microcontroller 60 is integral in the circuitry 48 and does not require an interface for external data. Data and programs used by the microcontroller 60 or recorded by the physiologic monitor are stored in SRAM 62 and NVM 64.

Figure 4:
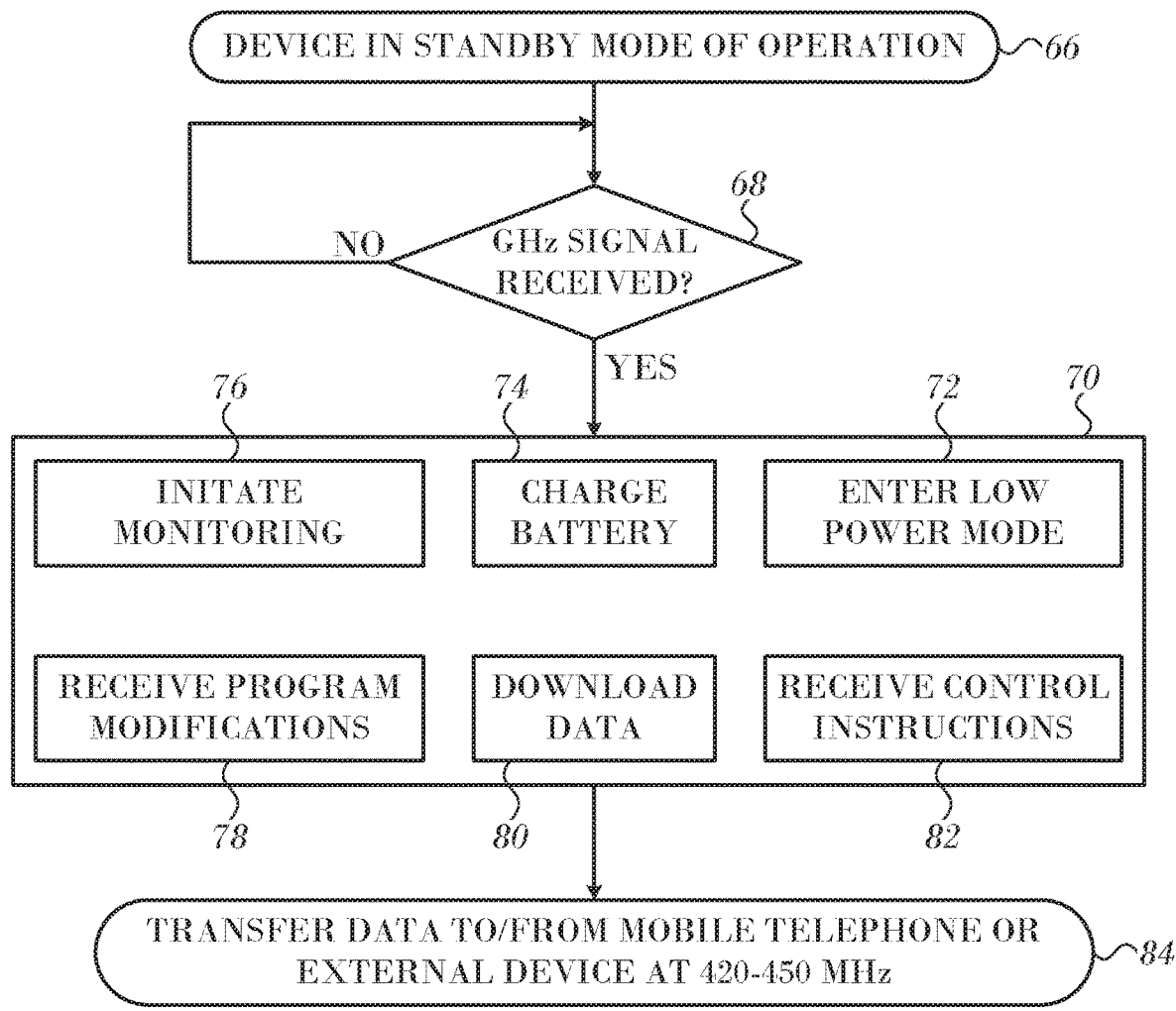
FIG. 4 is a flow chart of a method of operating an injectable monitor in accordance with an embodiment of the invention.

Reference is now made to FIG. 4, which is a high level flow chart of a method of operating an injectable monitor in accordance with an embodiment of the invention. It is assumed that at initial step 66 the device is in a standby mode of operation. However, the method may be applied, mutatis mutandis, to alter any mode of operation of the device. For example, it may be desired to cause the device to cease active operation and to enter an inactive or hibernating mode. As another example, the method may cause the device to initiate or discontinue battery charging, or physiologic monitoring for a set time interval, such as one hour.

At delay step 68 the method awaits a triggering signal, typically in the GHz range, e.g., 2.4 GHz, from a transmitter in proximity with the device, typically within 5 cm. The device power consumption is 5 mA average TX/RX current and 300 nA average SLEEP/SNIFF current pulse of short duration and having sufficiently low power so as to avoid interference with military and governmental systems that extensively use this frequency range. In addition, the signal is digitally encoded to create a unique signature for the device, and thereby avoid spurious activations and interference with similar devices that may be nearby, e.g., in a hospital ward. Any suitable conventional communications protocol may be used to command the device.

Next, at step 70 the mode of operation is changed in response to the ISM band signal. Step 70 includes any of blocks 72, 74, 76, 78, 80, 82, or a combination thereof. The items in step 70 are exemplary, and many other operations of the monitor may be initiated or regulated in response to the signal. Block 72 indicates the operation of initiating monitoring. Block 74 represents a command to charge the device battery. Block 72 represents a command to cease active operation and enter low power mode. Block 78 indicates installation of a program modification. Block 80 represents a command to download data. Block 82 indicates transmission of control instructions, such as resetting the device, clearing files, and other maintenance tasks and a wakeup pulse in the GHZ range as described above.

At final step 84 data is transferred to or from an external device. The external device can be a mobile telephone, optionally linked to an auxiliary transmitter or receiver. The transfer is conducted at a different frequency than the signal received at delay step 68, typically in the range of 400-450 MHz.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A physiologic monitoring device comprising:
a housing that is adapted for implantation in a body of a patient and containing:
a communication interface;
a sensor responsive to a physiologic event;
a processor, which is configured to detect and record signals from the sensor and to wirelessly communicate via the communication interface with a transmitter and a receiver that are disposed outside the housing, and to receive via the communication interface transmissions of commands and data from the transmitter;
a memory accessible to the processor;
a battery for powering the device,
wherein the device operates in one of a standby mode and an active mode that consumes more power from the battery than the standby mode, and wherein the transmissions comprise:
control signals that are transmitted by the transmitter at a first frequency in a first range of 1-10 GHz; and
transfers of recorded data from the sensor to the receiver at a second frequency in a second range of 400-450 MHz;
wherein the housing is adapted to be implanted by injection into subcutaneous tissue of the patient, or is adapted to be secured within a wall of the left ventricle of the heart of the patient.

2. The device according to claim 1, wherein the control signals comprise a wakeup command to terminate the standby mode and to begin operation in the active mode.

3. The device according to claim 1, wherein the control signals comprise a command to enter the standby mode of operation.

4. The device according to claim 1, wherein the control signals comprise a command to receive program modifications.

5. The device according to claim 1, wherein the control signals comprise a command to initiate or terminate monitoring of signals from the sensor.

6. The device according to claim 1, wherein the control signals comprise a signal to transfer data from the memory to the receiver.

7. The device according to claim 1, wherein the first frequency is 2.4 GHz.

8. The device according to claim 1, wherein the second range is 402-MHz-405-MHz.

9. The device according to claim 1, wherein the second range is 433-MHz-434-MHz.

10. The device according to claim 1, wherein the physiologic event is an electrical signal from a heart of the patient.

11. The device according to claim 1, further comprising battery charging circuitry linked to the battery.

12. The device according to claim 11, wherein the control signals comprise a command to activate the battery charging circuitry to charge the battery.

13. A method of physiologic monitoring comprising:
providing a device that is adapted for implantation in a body of a patient, comprising:
a housing;
a communication interface;
a sensor responsive to a physiologic event;
a processor, which is configured to detect and record data from the sensor;
a memory accessible to the processor; and a battery for powering the device;
implanting the device by injection into subcutaneous tissue of the patient, or securing the device to a wall of the left ventricle of the heart of the patient;
operating the device in one of a standby mode and an active mode that consumes more power from the battery than the standby mode;
wirelessly exchanging signals via the communication interface with a transmitter and a receiver that are disposed outside the housing, wherein wirelessly exchanging signals comprises:
when the device is in the standby mode receiving control signals from the transmitter at a first frequency in a first range of 1-10 GHz to terminate the standby mode and to begin operation in the active mode;

when the device is in the active mode at a second frequency transferring the recorded data in a second range of 400-450 MHz from the sensor to the receiver; and receiving program instructions from the transmitter to operate the processor.

14. The method according to claim 13, further comprising: responsively to the control signals charging the battery by activating battery charging circuitry.

15. The method according to claim 13, further comprising: responsively to the control signals terminating the active mode and entering the standby mode of operation.

16. The method according to claim 13, further comprising: responsively to the control signals receiving program modifications.

17. The method according to claim 13, further comprising: responsively to the control signals initiating or terminating monitoring of signals from the sensor.

18. The method according to claim 13, further comprising: responsively to the control signals transferring the recorded data from the memory to the receiver.

19. The method according to claim 13, wherein the first frequency is 2.4 GHz.

20. The method according to claim 13, wherein the second range is 402-MH-405-MHz.

21. The method according to claim 13, wherein the second range is 433-MHz-434-MHz.

22. The method according to claim 13, wherein the physiologic event is an electrical signal from a heart of the patient.

* * * * *

UNITED STATES PATENT AND TRADEMARK OFFICE
CERTIFICATE OF CORRECTION

| | |
|---|---|
| PATENT NO. | : 10,736,509 B2 |
| APPLICATION NO. | : 16/048542 |
| DATED | : August 11, 2020 |
| INVENTOR(S) | : Assaf Govari et al. |

It is certified that error appears in the above-identified patent and that said Letters Patent is hereby corrected as shown below:

On the Title Page

In Item (57), under "ABSTRACT", in Column 2, Line 7, delete "Transmissions" and insert -- transmissions --, therefor.

Signed and Sealed this
Thirteenth Day of December, 2022

Katherine Kelly Vidal
*Director of the United States Patent and Trademark Office*